United States Patent [19]

Nagels et al.

[11] Patent Number: 5,763,275
[45] Date of Patent: Jun. 9, 1998

[54] METHOD AND APPARATUS FOR CO-CULTURING CELLS

[75] Inventors: Hans-Otto Nagels, Bovenden; Dieter Schröder, Osterode; Eckart Kopowski, Braunschweig, all of Germany

[73] Assignee: Heraeus Instruments GmbH, Hanau, Germany

[21] Appl. No.: 676,311

[22] PCT Filed: Oct. 25, 1995

[86] PCT No.: PCT/EP95/04190

§ 371 Date: Sep. 9, 1996

§ 102(e) Date: Sep. 9, 1996

[87] PCT Pub. No.: WO96/16161

PCT Pub. Date: May 30, 1996

[30] Foreign Application Priority Data

Nov. 18, 1994 [DE] Germany ............... 44 41 119.7

[51] Int. Cl.$^6$ ............... C12N 5/00; C12M 3/04; C12M 3/06
[52] U.S. Cl. ............ 435/373; 435/297.1; 435/304.1; 435/305.2; 435/305.3
[58] Field of Search ............... 435/401, 373, 435/297.1, 297.5, 304.1, 304.3, 305.1

[56] References Cited

U.S. PATENT DOCUMENTS

| | | | |
|---|---|---|---|
| 4,661,455 | 4/1987 | Hubbard | 435/401 |
| 5,173,225 | 12/1992 | Range et al. | 264/45.5 |

FOREIGN PATENT DOCUMENTS

92/22634  12/1992  WIPO.

OTHER PUBLICATIONS

Falkenberg et al., A simple and inexpensive high density dialysis tubing cell culture system for the in vitro production of monoclonal antibodies in high concentration, J. Immunol. Methods, vol. 165, pp. 193–206, 1993.

*Primary Examiner*—David M. Naff
*Assistant Examiner*—Janet M. Kerr
*Attorney, Agent, or Firm*—Workman, Nydegger & Seeley

[57] ABSTRACT

The method relates to the co-culturing of two cell cultures in two cell culture chambers such that the cellular products produced by the co-cultured cells are exchanged between the two cell culture chambers. The apparatus for culturing the cells contains two cell culture chambers separated by a microfiltration membrane which is permeable to medium, gases, and cellular products, and is impermeable to cells. A culture medium supply chamber is adjacent to and separated from the first cell culture chamber by a dialysis membrane which is permeable to medium and gases. The exterior portion of the second cell culture contains a gas-exchange membrane which allows gas exchange between the apparatus and the environment. The apparatus can be in a modular form where the first and second cell culture chambers form one module which is detachable from the culture medium supply chamber which forms the second module. The method and apparatus allows the exchange of media, gases, and cellular products between the two cell cultures while preventing direct contact of the two cell cultures.

8 Claims, 2 Drawing Sheets

METHOD AND APPARATUS FOR CO-CULTURING CELLS

BACKGROUND OF THE INVENTION

The invention relates to a method of cell culturing in which a cell product released from a first cell culture is transported into a second cell culture and is integrated with the cells of the second cell culture.

This type of method may be used, for example, to transfer a cell product, such as a vector, from a first cell culture to a second cell culture, such as a lymphocyte culture. For this purpose, the first cell culture, for example a murine cell culture, which produces the vector of interest, will be cultured in a culture vessel. The cells will then be separated by centrifugation from the released vectors and the supernatant containing the vector will be added to the second cell culture, the lymnphocytes. In order to avoid thinning the lymphocyte culture too much, the addition of vectors is repeated several times. It is also necessary to keep in mind that the half-life of the vectors lasts only 10 minutes, which, on the one hand, requires working as quickly as possible, and on the other hand, excludes the addition of large quantities of the vector in a single operation. For this reason, the known methods are slow.

In addition, because of the large amount of equipment required and numerous steps involved in using the known methods, there is a constant risk of contamination to the cell culture.

Moreover, the invention relates to a culture vessel for cell cultures having a first cell culture chamber for the reception of a first cell culture, having a supply chamber for the reception of a culture medium, having a dialysis membrane between the cell culture chamber and the supply chamber by means of which the nutrients are transported into the cell culture chamber and the metabolic products of the cell culture are removed from the cell culture chamber, and having a gas-exchange membrane that forms at least part of the external portion of the culture vessel.

This type of culture vessel is known from DE-Al 42 29 325. It describes a culture vessel which has a supply chamber and at least one cell culture chamber within a substantially hollow, cylindrical plastic housing. The two chambers are separated from one another by a flat, semipermeable dialysis membrane. The culture medium is transported from the supply chamber into the cell culture chamber and the metabolic products removed from the cell culture chamber by means of the dialysis membrane. The end surface of the plastic tube facing the cell culture chamber is closed by a silicone foil approximately 0.5 mm in diameter that serves as a gas-exchange membrane. The silicone foil is permeable to oxygen and carbon dioxide, but impermeable to liquids and bacteria.

The known culture vessel is able to rotate on a roller-rotator device on its long axis, by which means mixing of the liquid culture medium and cell culture plaque takes place in the cell culture chamber Oxygen supply to the cell culture is effected through the direct passage of oxygen via the gas-exchange membrane to the cell culture plaque as well as indirectly via prior passage to the nutrient solution, from which it reaches the cell culture chamber via the dialysis membrane.

The known culture vessel may have several cell culture chambers. It is consequently capable of culturing one or more cell cultures. The previously described method, referred to as co-culturing, however, is not feasible by this means.

SUMMARY OF THE INVENTION

It is the object of this invention to offer a method for which the risk of contamination during transfer of a cell product to a second cell culture is reduced and which permits a high yield and rate of production. Furthermore, it is the object of this invention to provide a culture vessel for cell cultures, in which a co-culturing method may be implemented with a minimum of labor.

With regard to method, the object is solved in the context of the convention by the previously mentioned method, in that the first and second cell cultures are contiguous, and in that they are separated by a membrane which is impermeable to the cells of the cell culture, but permeable to the cell product, and in that the cell product is transported into the second cell culture via the membrane. Given the fact that the cell cultures are separated from one another only by the membrane, which is permeable to the cell product of the first cell culture, a continuous transfer of the cell product from one cell culture to the other is made possible. Transfer of the cell product occurs without a loss of time. The impetus for the transfer to the second cell culture chamber could, for example, be the equalization of concentration. A prolonged work period, such as for the separation of the cell product by centrifugation, and subsequent addition to the second cell culture is not required. The danger of accidental infection of the cell cultures is thereby reduced. At the same rate at which the cell product is released from the first cell culture, it is drawn through the membrane and transported into the second cell culture.

The second cell culture can also be a cell-free medium. In this case, the cell product can be concentrated and removed without cellular biomass. The second cell culture can also contain a second cell line, with which the cell product of the first cell line may be integrated.

Of proven value is a method in which the first and the second cell cultures are cultured in a shared culture medium, where they are separated from the culture medium by a dialysis membrane that is permeable to the nutrients. This method enables a continuous transfer of the cell product to the second cell culture over an extended period. As needed, the culture medium will be exchanged. The culture medium is separable from the cell cultures by means of a semipermeable membrane that is permeable to the nutrients and the metabolic products of the cell cultures.

It has proven to be particularly advantageous to culture the first and the second cell culture in a culture vessel that is sealed off from the outside. The sealed culture vessel prevents contamination of the cell cultures. The culturing can be done in a roller bottle culture vessel. The rotating motion facilitates the mixing of the cell cultures and culture medium.

Of proven value is a method in which the first and/or the second cell culture is supplied with oxygen via a gas-exchange membrane. This facilitates a contamination-free supply of oxygen to the cells. It is not required that both cell cultures have direct contact with the gas-exchange membrane. The supply of oxygen can also occur indirectly through the passage of oxygen into one cell culture or into the culture medium.

With regard to the device, the above-mentioned object is solved by the invention previously described, in that there is a second cell culture chamber for the reception of a second cell culture, which is separated from the first cell culture chamber by a filtration membrane that is impermeable for the cells of the first and second cell culture.

Because the first cell culture chamber is separated from the second cell culture chamber by a filtration membrane, a transfer of the cell products from the first cell culture chamber is possible without fear of contaminating one or the other cell cultures. The transfer of cell products from one cell culture chamber to the second cell culture chamber can occur continuously. The invented culture vessel permits simultaneous culturing of the two cell cultures side by side, for example, in a common culture medium. As the filtration membrane is impermeable to both cell cultures the contamination of the cell cultures with cells of the other cell culture is excluded.

Of proven value is an embodiment of the culture vessel in which the filtration membrane is a microfiltration membrane. Microfiltration membranes are available commercially. The diameter of the pores of the microfiltration membrane can easily be synchronized with the size of the cell product. It is also of proven value to insert a dialysis membrane within the filtration membrane.

It is an advantage to have a culture vessel in which the second cell culture chamber is bounded, on the one hand, by a filtration membrane, and on the other hand, by a gas-exchange membrane. In that the second cell culture chamber is bounded by the gas-exchange membrane, the cell culture is especially well supplied with oxygen.

It is preferable for a culture vessel to have the dialysis membrane, the filtration membrane, and the gas-exchange membrane constructed substantially on the same plane. Such membranes are easy to manufacture. The arrangement lends itself to a modularly-constructed culture vessel. In the case of at roller bottle culture vessel, the cell culture chambers could, for example, be arranged side by side along the long axis of the culture vessel. However, the arrangement of one behind the other has proven very effective in being especially easy to produce.

Especially advantageous is an embodiment of the culture vessel which have a supply module containing the supply chamber and a production module containing the first and second cell culture chamber, and where the modules are detachable from one another. The supply chamber is conveniently provided with a one-way opening for pouring in the supply medium. The modular construction of the culture vessel facilitates replacement of the individual modules. The cell culture chambers are conveniently provided with sealable openings. These may be used for filling or removal of the cell cultures. These openings could, for example, be embodied as septum or so-called Luer-Lock closures.

BRIEF DESCRIPTION OF THE DRAWINGS

One sample embodiment of the invention is shown in the figures and will be further explained below. The figures show in detail FIG. 1 a culture vessel, represented schematically, having a co-culturing module with two cell culture chambers

DETAILED DESCRIPTION OF THE INVENTION

Figure 1:
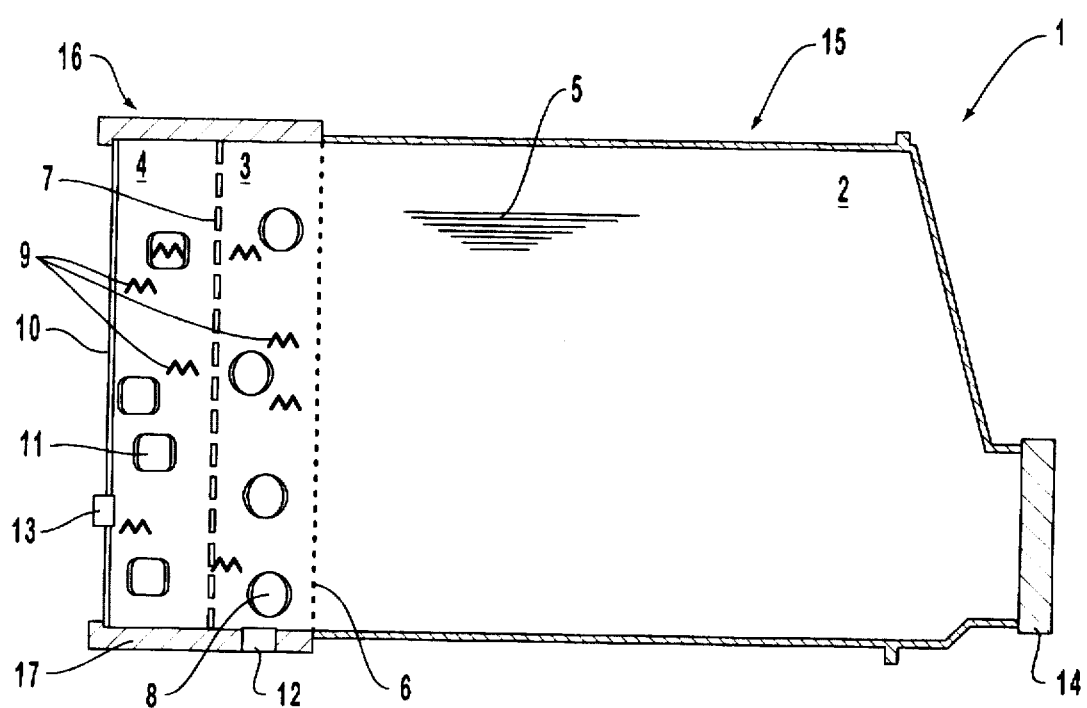

The entire culture vessel is represented in FIG. 1 by the number 1. The culture vessel 1 comprises three chambers, a supply chamber 2, a first cell culture chamber 3 and a second cell culture chamber 4. The supply chamber 2 is, with the exception of an air bubble, filled with a culture medium 5 for the cell cultures. Cell culture chamber 3 is divided from the supply chamber 2 by a flat dialysis membrane 6. Cell culture chamber 4 is separated from cell chamber 3 by a microfiltration membrane 7. Cell culture chamber 4 is closed off from the outside by a gaspermeable silicone membrane 10, with knobs which turn inward, are hollow and open outwards for improved gas supply (see FIG. 2 below).

The cells in exemplary cell culture chamber 3 are murine fibroblasts 8. These release a cell product, namely a vector 9. The cells of the cell culture in exemplary cell culture chamber 4 are lymphocytes 11. These are able to incorporate into the cell nucleus the vector 9 released from the murine fibroblasts.

For filling and removing the cell cultures or the cell product, the end surface of the roller bottle-type culture vessel 1, which has a gas-exchange membrane 10, is provided with so-called Luer-Lock seals 13, and in the area of cell culture chamber 3, with a so-called septum 12 in the cylinder housing surface of the culture vessel 1. For filling the supply chamber 2 with the culture medium 5, there is a screw-cap 14 located on the front side of the supply chamber 2. Otherwise, the culture vessel 1 is closed on all sides.

The culture vessel 1 comprises two modules, a supply module 15 with the supply chamber 2, and a co-culturing module 16, which contains the two cell culture chambers, 3; 4. The two modules 15;16 are held together by a water-tight snap-lock 17 and are detachable.

To give a more detailed explanation of the method used in the invention, there follows a description of a method of gene therapy using recombinant lymphocytes with the aid of the culture vessel 1 shown in FIG. 1.

The lymphocytes 11 are human lymphocytes with a genetic defect, for example, a disruption in the production of an enzyme required for the human organism. The murine fibroblasts 8 contain a retroviral vector with a gene which can replace the defective gene in the lymphocytes. They continuously release the vector 9, a virus or virus envelope. As the murine fibroblasts 8 grow tightly adherent, cell culture chamber 3 is provided with an appropriate carrier, for example, microcarriers or a porous stationary matrix.

To implement the gene therapy, two cell lines are cultured simultaneously or phased-in separately into cell chambers 3 and 4. The invented method will henceforth be referred to as the "co-culturing method." A phasing-in culturing method can, for example, be sensible when in order to achieve an optimal "co-culturing" of both cell lines 8; 11, one requires a head start on the other, or when the cell cultures need different culture mediums for optimal growth.

In the "co-culturing" stage, both cell lines 8; 11 are supplied simultaneously with nutrients via the semipermeable membrane 6. For this purpose, the pore diameter of the dialysis membrane 6 is set at a MWCO-value (Molecular Weight Cut-Off) of approximately 2 kilodaltons, so that it is permeable both to the nutrients of the culture medium 5 and the metabolic products of the cells 8 and 11, but not to the murine fibroblasts 8 or the vector 9. In this way, the metabolic products can be removed via the dialysis membrane 6 from the cell lines 8; 11 and simultaneously the vector 9 can be concentrated in the co-culturing module 16. Via the gas-permeable membrane 10, the murine fibroblasts 8 and the lymphocytes 11 are supplied with oxygen. The murine fibroblasts 8, for which the cell density should not be too high, and therefore should be set at less than $10^6$ cells/ml, continuously release the vector 9. An approximately 0.2 µm pore diameter should be selected for the microfiltration membrane 7 so that the vector 9 can pass through the membrane, but not the cells of either cell line 8; 11. The result is a continuous transfer of the vector 9 from cell culture chamber 3 into cell culture chamber 4. There, the intact gene, or a portion thereof, is continually flushed into the lymphocytes 11. This continuous method is especially advantageous in the case where the vector 9 has only a short half-life, perhaps only a few minutes.

Because of the short distances for the vector 9 and its rapid and continuous availability for the defective lymphocytes, there is a high rate of infection. The method runs in a closed system. Contamination of the medium 5 or the cell cultures 8; 11 is consequently avoided.

A further embodiment of the method of the invention is the case when cell culture chamber 4 is not filled with a cell culture. A dialysis membrane serves as a filtration membrane 7 between cell culture chamber 3 which contains the murine fibroblasts 8, and cell chamber 4. Otherwise, the method and the culture vessel conform to the explanation and the embodiment explained above. By this method a cell-free harvest of the vector 9 from cell culture chamber 4 is possible.

In the following, an embodiment of a "co-culturing module" will be explained in more detail using FIG. 2.

Figure 2:
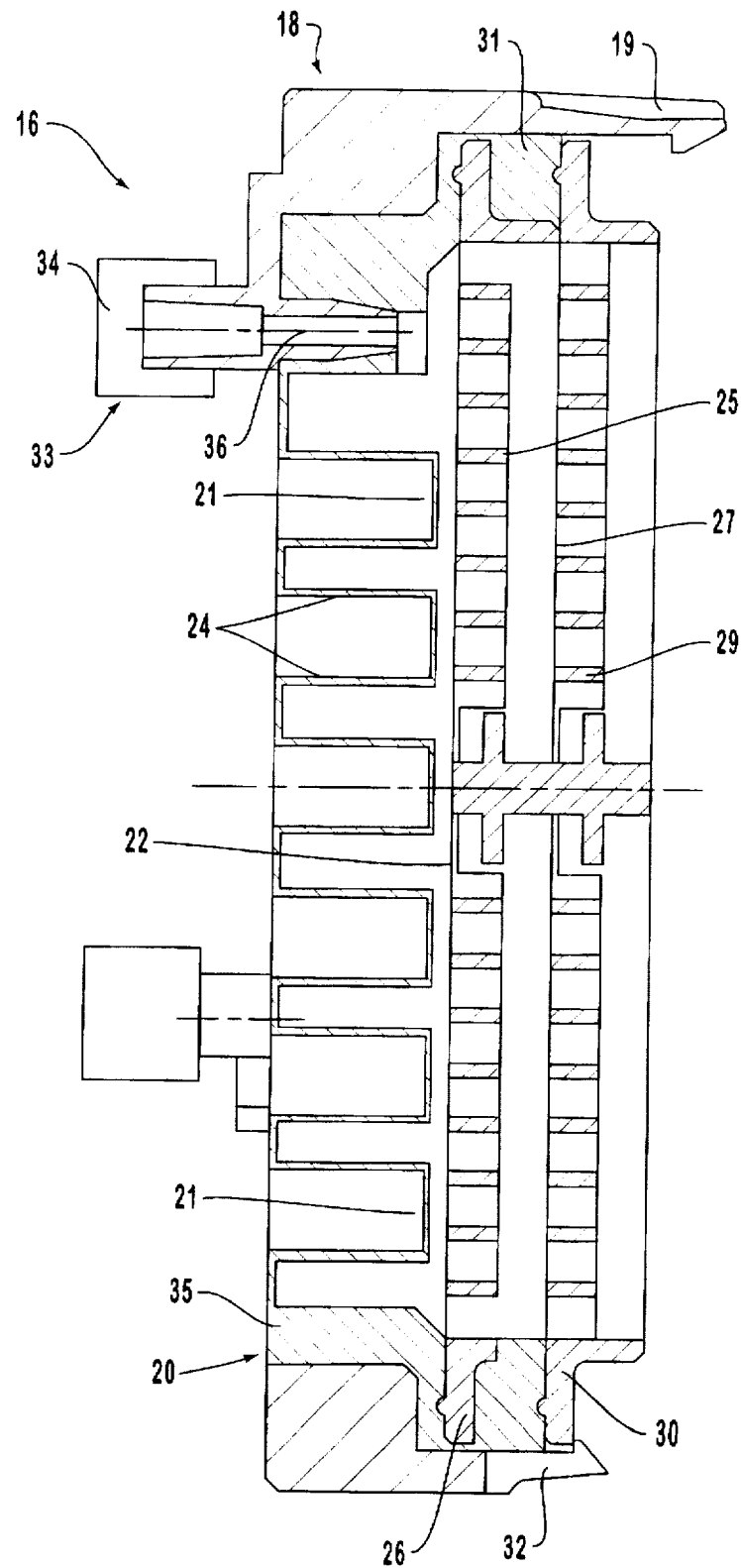
FIG. 2 shows a cross-section of the portion of the co-culturing module indicated in FIG. 1 in the form of a technical drawing.

FIG. 2 shows a portion of a co-culturing module 16 enlarged by ratio of 2:1. The co-culturing module 16 is formed from a circular span ring 18 made of durable polycarbonate, on which are molded snap hooks 19, by means of which the co-culturing module 16 can be joined with the supply module 15. A silicone component 20 is inserted inside the span ring 18. The silicon component has areas of varying thickness. The thicker outer rim of the silicon component 20 is shown as number 35 in FIG. 2, and that of the area covering the span ring is shown as number 18, which has a thickness of approximately 0.5 mm, and that which serves as the gas-exchange membrane is shown as number 24. In order to enlarge the gas-exchange surfaces, the gas-exchange membrane 24 is provided with knobs opening outwards. Between the silicon component 20 and the dialysis membrane 6, a first cell culture chamber 23 is formed. Cell culture chamber 23 (the corresponding cell culture chamber is designated as 4 in FIG. 1) holds a volume of approximately 35 ml and serves, for example, for the reception and culturing of human lymphocytes containing defective genes. The micro-filtration membrane 22 rests against the first lattice 25, whose rim 26 rests upon the silicone component 20. The cross pieces of the lattice 25 serve, simultaneously, as a mixing element during rotation of the co-culturing module 16.

A second cell culture chamber 28 is bounded by microfiltration membrane 22 on one side and a dialysis membrane 27 on the other side. It has a volume of approximately 5 ml and serves for the reception of murine fibroblasts (the corresponding cell culture chamber is designated as 3 in FIG. 1) dialysis membrane 27 rests against a second lattice 29 whose rim 30 rests upon a middle silicone ring 31. The middle silicone ring provides the thickness between the lattices, 25; 29 on the one hand, and the septum for the cell culture chamber 28, on the other hand. The silicone component 20, the lattices 25; 29, the membranes 22; 27, and the middle ring 31 are held together by the snap hooks 32, which are evenly distributed around the span ring 18.

For filling, emptying, inoculation or removal of samples from the cell culture chamber 23, Luer-lock closures 33 have been mounted on the span ring 18. The opening of the Luer-Lock closures 33 into cell chamber 23 are sealed water-tight by means of caps.

We claim:

1. A method of cell culturing comprising:
   (a) obtaining a cell culturing vessel comprising:
      (i) a first cell culture chamber and a second cell culture chamber separated by a microfiltration membrane, for the reception of a first and a second cell culture, respectively, wherein said microfiltration membrane allows exchange of culture medium, gases, selected cellular products, and metabolic waste products while preventing exchange of cells between said first and second cell culture chambers;
      (ii) a culture medium supply chamber adjacent to said first cell culture chamber, said culture medium supply chamber and said first cell culture chamber are separated by a dialysis membrane wherein said dialysis membrane allows exchange of culture medium, gases, and metabolic waste products, while preventing exchange of selected cellular products and cells between said first cell culture chamber and said culture medium supply chamber; and
      (iii) a gas-exchange membrane that forms at least a part of the exterior wall of said second cell culture chamber wherein said gas-exchange membrane allows the exchange of gases between said second cell culture chamber and the surrounding atmosphere;
   (b) culturing a first cell culture in said first cell culture chamber; and
   (c) simultaneously culturing a second cell culture in said second cell culture chamber.

2. The method of cell culturing described in claim 1 wherein the first and the second cell culture chambers are components of a roller bottle cell culture vessel.

3. The method of cell culturing described in claim 1 wherein the first and second cell cultures are supplied with oxygen which passes through said gas-exchange membrane.

4. A cell culture vessel comprising:
   (a) a first cell culture chamber and a second cell culture chamber separated by a microfiltration membrane, for the reception of a first and a second cell culture, respectively, wherein said microfiltration membrane allows the exchange of culture medium, gases, selected cellular products, and metabolic waste products while preventing exchange of cells between said first and second cell culture chambers;
   (b) a culture medium supply chamber for the reception of a culture medium, said culture medium supply chamber is adjacent to said first cell culture chamber, and separated from said first cell culture chamber by a dialysis membrane, wherein said dialysis membrane allows exchange of culture medium, gases, and metabolic waste products while preventing exchange of selected cellular products and cells between said first cell culture chamber and said culture medium supply chamber; and
   (c) a gas-exchange membrane which forms at least a part of the exterior wall of said second cell culture chamber wherein said gas-exchange membrane allows the exchange of gases between said second cell culture chamber and the surrounding atmosphere.

5. The culture vessel as described in claim 4 wherein the second cell culture chamber is bounded by the microfiltration membrane and the gas-exchange membrane.

6. The culture vessel as described in claim 4 wherein the dialysis membrane, microfiltration membrane, and the gas-exchange membrane are substantially aligned parallel to one another.

7. The culture vessel as described in claim 4 wherein the first and second cell culture chambers form a unitary structure which is capable of being detached from said culture medium supply chamber.

8. The culture vessel as described in claim 4 wherein the first and second cell culture chambers have sealable openings.

* * * * *